US011293963B2

(12) United States Patent
Kerselaers et al.

(10) Patent No.: US 11,293,963 B2
(45) Date of Patent: Apr. 5, 2022

(54) DEVICE FOR ELECTROMAGNETIC STRUCTURAL CHARACTERIZATION

(71) Applicant: NXP B.V., Eindhoven (NL)

(72) Inventors: Anthony Kerselaers, Herselt (BE); Axel Nackaerts, Haasrode (BE)

(73) Assignee: NXP B.V., Eindhoven (NL)

( * ) Notice: Subject to any disclaimer, the term of this patent is extended or adjusted under 35 U.S.C. 154(b) by 626 days.

(21) Appl. No.: 15/823,735

(22) Filed: Nov. 28, 2017

(65) Prior Publication Data
US 2019/0162766 A1    May 30, 2019

(51) Int. Cl.
*A61B 5/05* (2021.01)
*A61B 5/053* (2021.01)
(Continued)

(52) U.S. Cl.
CPC ........... *G01R 29/0814* (2013.01); *A61B 5/02* (2013.01); *A61B 5/05* (2013.01); *A61B 5/053* (2013.01);
(Continued)

(58) Field of Classification Search
CPC .......... A61B 5/05; A61B 5/0507–0522; A61B 5/053; A61B 5/0531–0533; G01N 27/72;
(Continued)

(56) References Cited

U.S. PATENT DOCUMENTS 3,789,834 A * 2/1974 Duroux ................ A61B 5/0535
600/407

5,469,861 A * 11/1995 Piscopo ................. A61B 5/103
340/573.7
(Continued)

FOREIGN PATENT DOCUMENTS

CN          103914946 A      7/2014
WO    WO 2016/166318 A1    10/2016

OTHER PUBLICATIONS

Darling, Chad Eric et al.; "Bioimpedance-Based Heart Failure Deterioration Prediction Using a Prototype Fluid Accumulation Vest-Mobile Phone Dyad: An Observational Study"; retrieved from the Internet https://cardio.imir.org/2017/e1: 18 pages (Oct. 31, 2017).
Silva, Ricardo Reis Marquest; "Measuring Impedance in Congestive Heart Failure"; Thesis—University Do Porto; 84 pages(Jul. 27, 2016).

*Primary Examiner* — Pascal M Bui Pho
*Assistant Examiner* — Farouk A Bruce

(57) ABSTRACT

One example discloses a device for electromagnetic structural characterization, including: a controller having an electromagnetic transmitter output and a communications interface; wherein the controller is configured to send a signal over the electromagnetic transmitter output that causes an electromagnetic transmitter to generate a first electrical field (E1) and a first magnetic field (H1); wherein the controller configured to receive over the communications interface a second electric field (E2) and a second magnetic field (H2) received by an electromagnetic receiver; wherein the first electrical field and the first magnetic field correspond to when the electromagnetic transmitter is at a first location proximate to a structure and the second electrical field and the second magnetic field correspond to when the electromagnetic receiver is at a second location proximate to the structure; and wherein the controller is configured to calculate an impedance based on the electric and magnetic fields interacting with the structure.

17 Claims, 4 Drawing Sheets

(51) Int. Cl.
*A61B 5/02* (2006.01)
*A61B 5/00* (2006.01)
*A61B 5/08* (2006.01)
*A61B 5/0205* (2006.01)
*G01R 29/08* (2006.01)
*G01N 27/72* (2006.01)
*H04B 5/00* (2006.01)
*G01N 27/02* (2006.01)

(52) U.S. Cl.
CPC .............. *A61B 5/48* (2013.01); *G01N 27/72* (2013.01); *G01R 29/0892* (2013.01); *H04B 5/0025* (2013.01); *A61B 5/0205* (2013.01); *A61B 5/0809* (2013.01); *G01N 27/028* (2013.01)

(58) Field of Classification Search
CPC .............. G01N 27/028; G01R 29/0814; G01R 29/0892; H04B 5/025; H04B 5/00–06; H04B 5/0006–0093
See application file for complete search history.

(56) References Cited

U.S. PATENT DOCUMENTS

| | | | |
|---|---|---|---|
| 7,725,178 B2 | 5/2010 | Chen et al. | |
| 8,306,621 B2 | 11/2012 | Kim et al. | |
| 9,197,986 B1 | 11/2015 | Kerselaers et al. | |
| 2004/0167420 A1* | 8/2004 | Song | A61B 5/053 600/547 |
| 2005/0177062 A1* | 8/2005 | Skrabal | A61B 5/0535 600/547 |
| 2007/0167879 A1* | 7/2007 | Cochran | A61B 5/11 600/595 |
| 2007/0238988 A1* | 10/2007 | Minai | A61B 5/062 600/424 |
| 2007/0273390 A1 | 11/2007 | Champion et al. | |
| 2009/0062637 A1 | 3/2009 | Hashimshony et al. | |
| 2015/0212026 A1 | 7/2015 | Pluta et al. | |
| 2016/0235334 A1* | 8/2016 | Nebuya | G01B 3/10 |
| 2017/0181658 A1 | 1/2017 | Dettmann et al. | |
| 2017/0126282 A1* | 5/2017 | Fromm | H04B 5/0037 |
| 2017/0182362 A1 | 6/2017 | McLeod et al. | |
| 2017/0199586 A1 | 7/2017 | Samuel et al. | |

\* cited by examiner

DEVICE FOR ELECTROMAGNETIC STRUCTURAL CHARACTERIZATION

The present specification relates to systems, methods, apparatuses, devices, articles of manufacture and instructions for structural characterization using electromagnetics.

SUMMARY

According to an example embodiment, a device for electromagnetic structural characterization, comprising: a controller having an electromagnetic transmitter output and a communications interface; wherein the controller is configured to send a signal over the electromagnetic transmitter output that causes an electromagnetic transmitter to generate a first electrical field (E1) and a first magnetic field (H1); wherein the controller configured to receive over the communications interface a second electric field (E2) and a second magnetic field (H2) received by an electromagnetic receiver; wherein the first electrical field (E1) and the first magnetic field (H1) correspond to when the electromagnetic transmitter is at a first location proximate to a structure and the second electrical field (E2) and the second magnetic field (H2) correspond to when the electromagnetic receiver is at a second location proximate to the structure; and wherein the controller is configured to calculate an impedance based on the electric and magnetic fields interacting with the structure.

In another example embodiment, the impedance is based on a distance between the first and second location proximate to the structure.

In another example embodiment, the distance corresponds to at least one of: a static structural orientation, a dynamic structural movement, a structural deformation, a body position, or a body movement.

In another example embodiment, the controller configures the fields to have a frequency that results in surface waves over an exterior surface of the structure.

In another example embodiment, the impedance is calculated based on absolute values of each field's signal strength.

In another example embodiment, a variation in the impedance over time is based on a change in the distance between the transmitter and receiver; and the change in the distance between the transmitter and receiver is interpreted as a change in a posture of the biological structure.

In another example embodiment, the impedance corresponds to physical motion either: after surgery, after a medical procedure; during sleep, while exercising, or during a routine activity.

In another example embodiment, the device further comprises a user interface; and the controller is configured to manipulate the user interface based on the impedance.

In another example embodiment, the impedance is based on a set of substances within the structure.

In another example embodiment, the substances correspond to at least one of: a liquid, a gas, a biological organ, a biological substance, or a tissue.

In another example embodiment, the structure is a biological structure; a variation in the impedance over time is based on a change in substances within the biological structure; and the change in the substances within the structure is based on a change in a health condition of an organ or tissue within the biological structure.

In another example embodiment, the controller configures the fields to have a frequency that penetrates the structure.

In another example embodiment, the impedance is calculated based on both amplitude and phase values of each field's signal strength.

In another example embodiment, the electromagnetic transmitter includes an antenna system configured to generate the first magnetic field (H1) from the first electrical field (E1).

In another example embodiment, the electromagnetic receiver includes an antenna system configured to receive the second electric field (E2) and the second magnetic field (H2).

In another example embodiment, the fields are NFEMI (near field electromagnetic induction) fields.

In another example embodiment, the communications link includes and passes signals representing the fields over either the electromagnetic transmitter or electromagnetic receiver.

In another example embodiment, either the electromagnetic transmitter or electromagnetic receiver include antennas that are capacitively, but not galvanically, coupled to the structure.

According to an example embodiment, a device for electromagnetic structural characterization: a controller having an electromagnetic receiver input and a communications interface; wherein the controller configured to receive over the communications interface a first electrical field (E1) and a first magnetic field (H1) generated by an electromagnetic transmitter; wherein the controller is configured to receive from the electromagnetic receiver input a second electrical field (E2) and a second magnetic field (H2) received by an electromagnetic receiver; wherein the first electrical field (E1) and the first magnetic field (H1) correspond to when the electromagnetic transmitter is at a first location proximate to a structure and the second electrical field (E2) and the second magnetic field (H2) correspond to when the electromagnetic receiver is at a second location proximate to the structure; and wherein the controller is configured to calculate an impedance based on the electric and magnetic fields interacting with the structure.

According to an example embodiment, an electromagnetic device for structural characterization: an electromagnetic transmitter configured to generate a first electrical field (E1) and a first magnetic field (H1); a communications interface configured to receive a second electrical field (E2) and a second magnetic field (H2) from an electromagnetic receiver; a controller coupled to the transmitter and communications interface; wherein the first electrical field (E1) and the first magnetic field (H1) correspond to when the electromagnetic transmitter is at a first location proximate to a structure and the second electrical field (E2) and the second magnetic field (H2) correspond to when the electromagnetic receiver is at a second location proximate to the structure; and wherein the controller is configured to calculate an impedance based on the electric and magnetic fields interacting with the structure.

The above discussion is not intended to represent every example embodiment or every implementation within the scope of the current or future Claim sets. The Figures and Detailed Description that follow also exemplify various example embodiments.

Various example embodiments may be more completely understood in consideration of the following Detailed Description in connection with the accompanying Drawings, in which:

Figure 1:
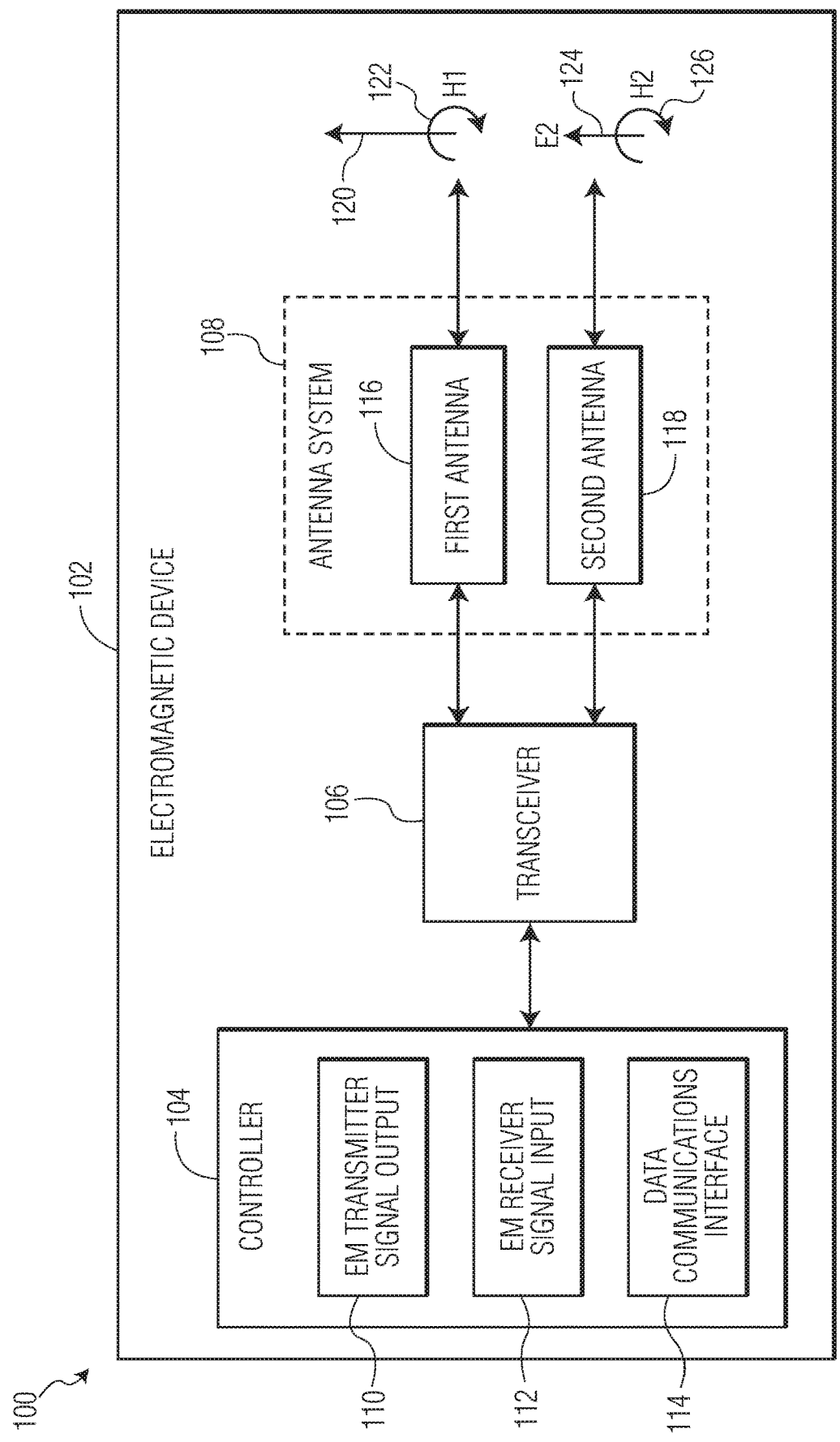
FIG. 1 is an example device for electromagnetic structural characterization.

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

Prediction and/or monitoring of health conditions and movements in a human or animal using different biological parameters is a useful pursuit. Health conditions may include: hearth rate, hearth rate variability, and blood pressure. Movements may include: body positions and walking, sitting or standing behavior.

These parameters can be monitored over a period of time and processed according algorithms that monitors and/or provides predictions of physical mobility and/or health issues.

Some example devices detect a cardiac or respiratory disease of a subject by means of monitoring sounds and the movements generated by the subject's lungs using external sensors placed on the subject's body.

Other example devices, monitor electrical activity using an implanted (i.e. internal) nanoelectrode array to determine an increased likelihood of the occurrence of a cardiac arrhythmia, myocardial ischemia, congestive heart failure and other diseased conditions.

Then there are devices that take a bio-impedance measurement using an implantable device for cardiac management containing a bio-impedance measurement circuit and some other sensors.

Studies of human and animal motion include measures from motion tracking systems, electrophysiology of muscle and brain activity, various methods for monitoring physiological function, and other behavioral and cognitive research techniques.

Different sensors (e.g. accelerometers) can localize positions in the time. The measured coordinates are then communicated to a central device. In clinical situations, the communication is standard done over wires. However sometimes also radio frequencies are used to communicate. The wireless systems use far field radiation systems like for example Bluetooth or Bluetooth low energy (BLE).

The signals are processed according an algorithm that provides the amount of movements and which movements. For example, the data can be used to define enough movements of some body parts after an operation to follow up the recovery, for example after replacement of a hip. Other applications are for example control of user interfaces like for example a smart screen. Tracking aids for fitness may greatly benefit from the proposed novel method. Intelligent care and alarm systems for elderly people or children to monitor sleep condition.

Now discussed are various example devices for monitoring and interpreting various structural characteristics (e.g. biological movements and health parameters) using near-field electromagnetic signals such as NFEMI (Near Field Electro-Magnetic Induction), on-body, surface waves, penetrating waves, and such which either follow the structure's surface and/or penetrate the structure.

Some of these example devices are configured to detect body orientations and/or movements such as muscle stretching, joint movement, and body posture. Other example devices are configured to detect health conditions such as when internal organ conductivity increases with pathology (e.g. disease causing water/liquid retention).

The example device, calculates a path impedance between at least two locations on the structure (e.g. human or animal) and monitors impedance fluctuations between these locations using near fields that are coupled to the structure.

The device may also re-use the near field signals to communicate between two or more measuring/monitoring devices placed at the different locations.

When the structure is a biological system, the device monitors and measures the passive electrical properties of the biological system. The passive electrical properties are determined by the observation of a biological tissue's electrical response to the application of near field signals. Thus the tissue is characterized as it were an electrical circuit composed by electrical components as resistors, capacitors, inductors and others. The measurement method derives parameters that are related to the change of postures and movements of body parts and/or with bio-impedance.

A cell in a biological system is the basic unit of living tissue. Its basic structure includes a bilayer membrane that separates an intracellular medium from an extracellular medium. Near-field measurements of the tissue's impedance from a few Hz to several tens of MHz (e.g. 10 MHz) results in a characterization of the cells condition.

Changing positions and volumes of tissues like muscles and bones also result in different impedances between positions. By monitoring the bio-impedance fluctuations over time different health conditions can be predicted.

For example, moving one arm behind the back of the body varies the impedance between a first location of an electromagnetic transmitter near the wrist and a second location of an electromagnetic receiver near the chest. This change can be detected and can initiate a warning when the person was supposed to be sleeping.

In another example, an increase in moisture content in lungs or a chest area may also be detected. In another example, weeks before a heart failure occurs, moisture content increases in the patient's chest area. This could be detected by the electromagnetic device. While the device can be used at clinics, perhaps more advantageously it can also be used at home where a patient can be monitored and warned in advance a condition that may happen.

FIG. 1 is an example 100 device for electromagnetic (EM) structural characterization 102. The electromagnetic device 102 include a controller 104, a transceiver 106 (i.e. EM transmitter and EM receiver), and an antenna system 108.

The controller 104 includes an EM transmitter signal output 110, an EM receiver signal input 112, and a data communications interface 114.

The antenna system 108 in some example embodiments includes a first antenna 116 and a second antenna 118. In transmit mode, the antenna system 108 transmits a first electrical field (E1) 120 and a first magnetic field (H1) 122. In reception mode, the antenna system 108 receives a second electric field (E2) 124 and a second magnetic field (H2) 126. In some example embodiments, these fields are NFEMI (near field electromagnetic induction) fields, and both antennas 116, 118 are small compared with the NFEMI wavelength. In one example embodiment, the first antenna 116 is a short loaded dipole antenna and the second antenna 118 is a loop antenna.

The data communications interface 114 in the electromagnetic device 102 communicates with other electromagnetic devices over a communications link that passes signals representing the fields between devices. In some example embodiments, these signals are also communicated over the transceiver 106 and the antenna system 108. In other example embodiments, these signals have a separate communications channel (e.g. wi-fi, Bluetooth, cellular, etc.).

The transceiver 106 (i.e. EM transmitter and EM receiver radio functions) in various example embodiments have a carrier frequency of 10 MHz. When the fields (E1, H1, E2, H2) are modulated with data, the modulation can be analogue or digital (e.g. frequency shift keying (FSK), quadrature amplitude modulation (QAM) or another type). Redundant frequency hopping or spread spectrum modulation may also be used to enhance the robustness of the data communication link.

The controller 104 is configured to send a signal over the electromagnetic transmitter signal output 110 that causes the transceiver 106 (e.g. an electromagnetic transmitter) to generate the first electrical field (E1) 120 and the first magnetic field (H1) 122. The controller 104 is also configured to receive over the data communications interface 114 the second electric field (E2) 124 and the second magnetic field (H2) 126 received by the transceiver 106 (e.g. an electromagnetic receiver).

The first electrical field (E1) 120 and the first magnetic field (H1) 122 correspond to when the electromagnetic transmitter is at a first location proximate to a structure and the second electrical field (E2) and the second magnetic field (H2) 126 correspond to when the electromagnetic receiver is at a second location proximate to the structure.

The controller 104 upon receipt of all fields calculates a path impedance based on the electric and magnetic fields interacting with the structure.

In various example embodiments the antenna system 108 is capacitively, but not galvanically, coupled to the structure. In some example embodiments, the structure may be: a container, a robot, a machine, a human body, an animal, a plant, or a biological tissue.

The impedance (e.g. path loss) calculated between the two different locations of the transmitter and receiver is based on a combination of the structure's impedance, the electromagnetic device's 102 impedance, and any free-space impedance between the electromagnetic device 102 and the structure.

In those example embodiments where the fields (E1, H1, E2, H2) are near-fields and are re-used for "data communication" as introduced above, just the first electric field (E1) 120 and the first magnetic field (H1) 122 can be used. The first transmitted magnetic field (H1) 122 may be independent of the first transmitted electric field (E1) 120. Specific variations in signal strength depend upon the transmitter and receiver's antenna design.

In contrast, when the fields (E1, H1, E2, H2) are near-fields and are used for structural characterization (e.g. structural/biological position and/or substance monitoring), both the first and second electrical fields (E1, E2) 120, 124 and the first and second magnetic fields (H1, H2) 122, 126 are used for calculating the impedance of the structure.

The fields (E1, H1, E2, H2) can be further optimized for either structural surface/contour characterization and/or structural interior characterization applications.

"Structural characterization" is herein defined to include both substances that make up a structure, such as a human body, and orientations and positions of elements that are part of the structure, such as body gestures, dynamic movements and static positions.

For near-fields, both electric fields (E1, E2) are bounded to the structure (i.e. the fields do not substantially radiate in free space around the structure).

Figure 2:
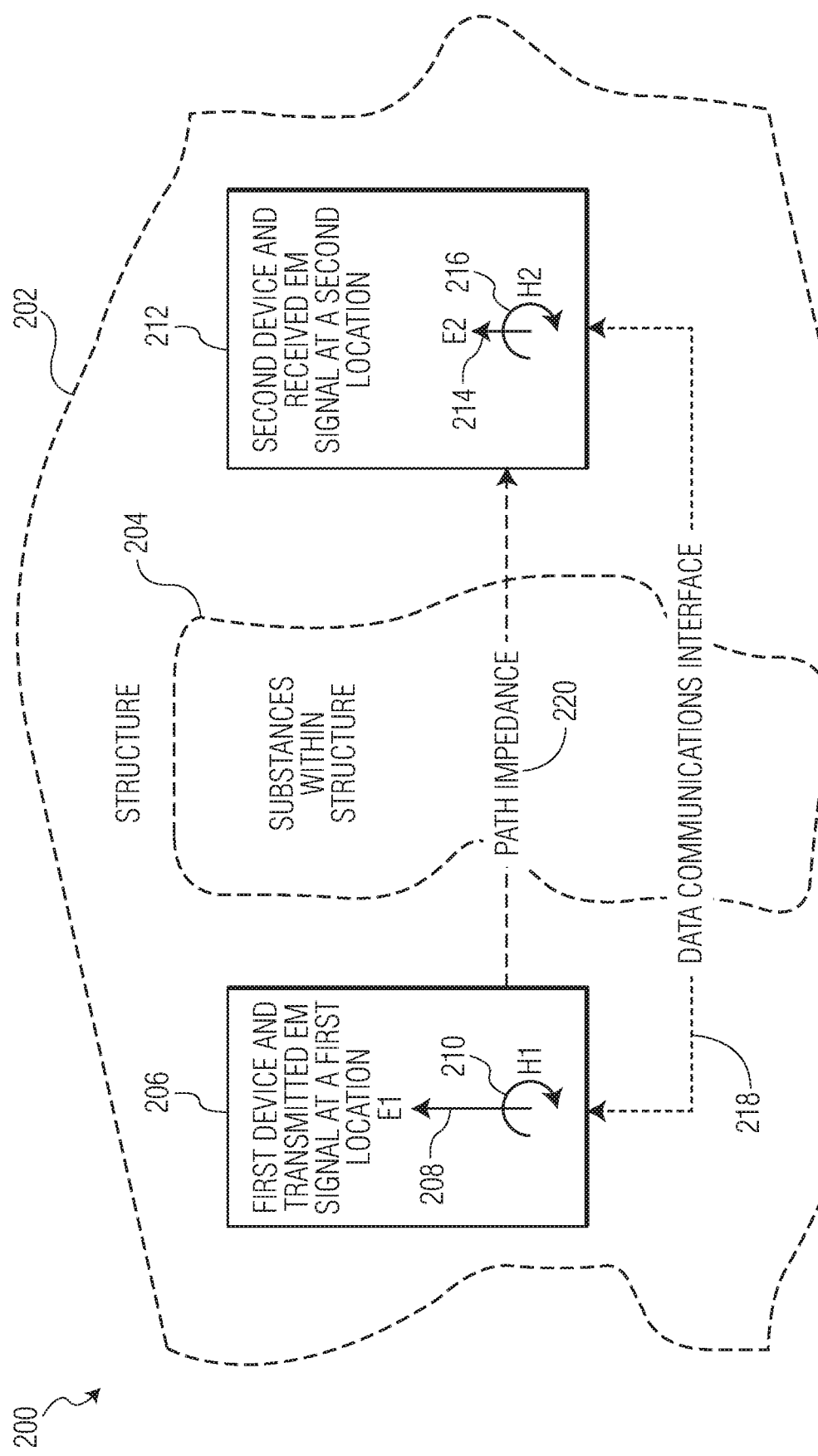
FIG. 2 is an example of first and second electromagnetic structural characterization devices on a structure.

FIG. 2 is an example 200 of first and second electromagnetic structural characterization devices on a structure. The example 200 includes a structure 202, substances within structure 204, a first device at first location 206 (e.g. EM transmitter), a second device at second location 212 (e.g. EM receiver), a data communications interface 218, a path impedance 220.

The first device at first location 206 generates a first electrical field (E1) 208 and a first magnetic field (H1) 210. The second device at second location 212 receives a second electrical field (E2) 214 and a second magnetic field (H2) 216.

Using these fields (E1, H1, E2, H2) both the structure's 202 position and movement and substances 204 (e.g. water retention, organ health, etc.) can be characterized.

For example the path impedance 220 can be interpreted as a distance between the first and second location proximate to the structure 202. The distance can correspond to at least one of: a static structural orientation, a dynamic structural movement, a structural deformation, a body position, or a body movement. In a medical application, physical movements can include monitoring patients: after surgery, after a medical procedure; during sleep, while exercising, or during a therapy activity.

A variation in the path impedance 220 over time is based on a change in the distance between the transmitter and receiver. This change in the distance can in some examples be interpreted as a change in a posture of a biological structure (e.g. a human body).

Distance and movement in some examples can be better monitored when the controller 104 configures the fields (E1, H1, E2, H2) to have a frequency that results in surface waves over an exterior surface of the structure 202. The path impedance 220 in some examples need only be calculated based on absolute values of each fields (E1, H1, E2, H2) signal strength.

In another application, one or more of the devices 206, 212 includes a user interface, and the controller 104 is configured to manipulate the user interface based on the path impedance 220.

In another set of example embodiments, the path impedance 220 is interpreted as characterizing and/or identifying the set of substances within the structure 202. Depending upon the structure 202 being monitored, the substances 204 can be: a liquid, a gas, a biological organ, a biological substance, or a tissue.

When the structure 202 is a biological structure, a variation in the path impedance 220 over time could be based on a change in one or more substances 204 within the biological structure. This change in the substances 204 within the structure 202 can be due to a health condition of an organ or tissue within the biological structure 202.

Substance 204 characterization in some examples can be better monitored/identified when the controller 104 configures the fields (E1, H1, E2, H2) to have a frequency that results in the fields (E1, H1, E2, H2) better penetrating the structure 202. In example applications for characterizing and/or identifying substances, the path impedance 220 is calculated based on both amplitude and phase values of each fields (E1, H1, E2, H2) signal strength.

Now discussed is a particular example impedance calculation wherein the structure 202 is a biological structure. Biological structures have a certain conductivity and permittivity characteristics which define the structure's bio-impedance.

From the first device at first location 206, the first electrical field (E1) 208 and the first magnetic field (H1) 210 are established. For frequencies below 50 MHz the first electrical field (E1) 208 is positioned perpendicular to the biological structure and as such is bound (i.e. electromagnetically coupled) to the structure. The first electrical field (E1) 208 generates the first magnetic field (H1) 210.

The transmit field impedance (Z1) at the first device at the first location 206 is:

$$Z1=E1/H1, \text{ where:}$$

Z1 impedance [ohm]
E1 electric field [V/m]
H1 magnetic field [A/m]

Both fields (E1, H1) are propagating along the bio-structure path and reduce in amplitude. The reduction in amplitude is different for each field type. The difference is depending on the bio-impedance of the bio-structure.

The received field impedance (Z2) at the second device at second location 212 is:

$$Z2=E2/H2, \text{ where:}$$

Z2 impedance [ohm]
E2 electric field [V/m]
H2 magnetic field [A/m]

A difference between the two impedances (Z1, Z2) is Zpath (i.e. the path impedance 220). For this biological application, Zpath is defined as:

$$Zpath=k \times Zbio, \text{ where:}$$

Zbio=Z1−Z2
Zbio bio-impedance [ohm]
k factor depending on the shape of or substances within the bio-structure In example embodiments wherein the path impedance 220 is interpreted as a distance (e.g. motion), a pathloss (i.e. absolute value of Zpath) is calculated as:

$$Pathloss=Vtx-RSSI, \text{ where:}$$

Pathloss in dB
Vtx=transmit voltage [dB µV]
RSSI=Received Signal Strength Indicator [dBµV]

RSSI is a result of an in-phase addition, enabled by the use of NFEMI, of the amplitude of the fields (E1, H1, E2, H2). This addition is realized in the antenna system 108. In some example embodiments, since separate values for the fields (E1, H1, E2, H2) are not available to the controller 104, only a loss difference (e.g. due to body movements) between the two locations is needed.

In example embodiments wherein the path impedance 220 is interpreted as characterizing and/or identifying the set of substances within the structure 202, the fields (E1, H1, E2, H2) are measured separately and a ratio between the fields (E1, H1, E2, H2) is calculated. To measure these fields (E1, H1, E2, H2) separately the first antenna 116 and the second antenna 118 are used.

Calculation of Zpath between two locations 206, 212 is determined as presented by the formulas above.

Figure 3:
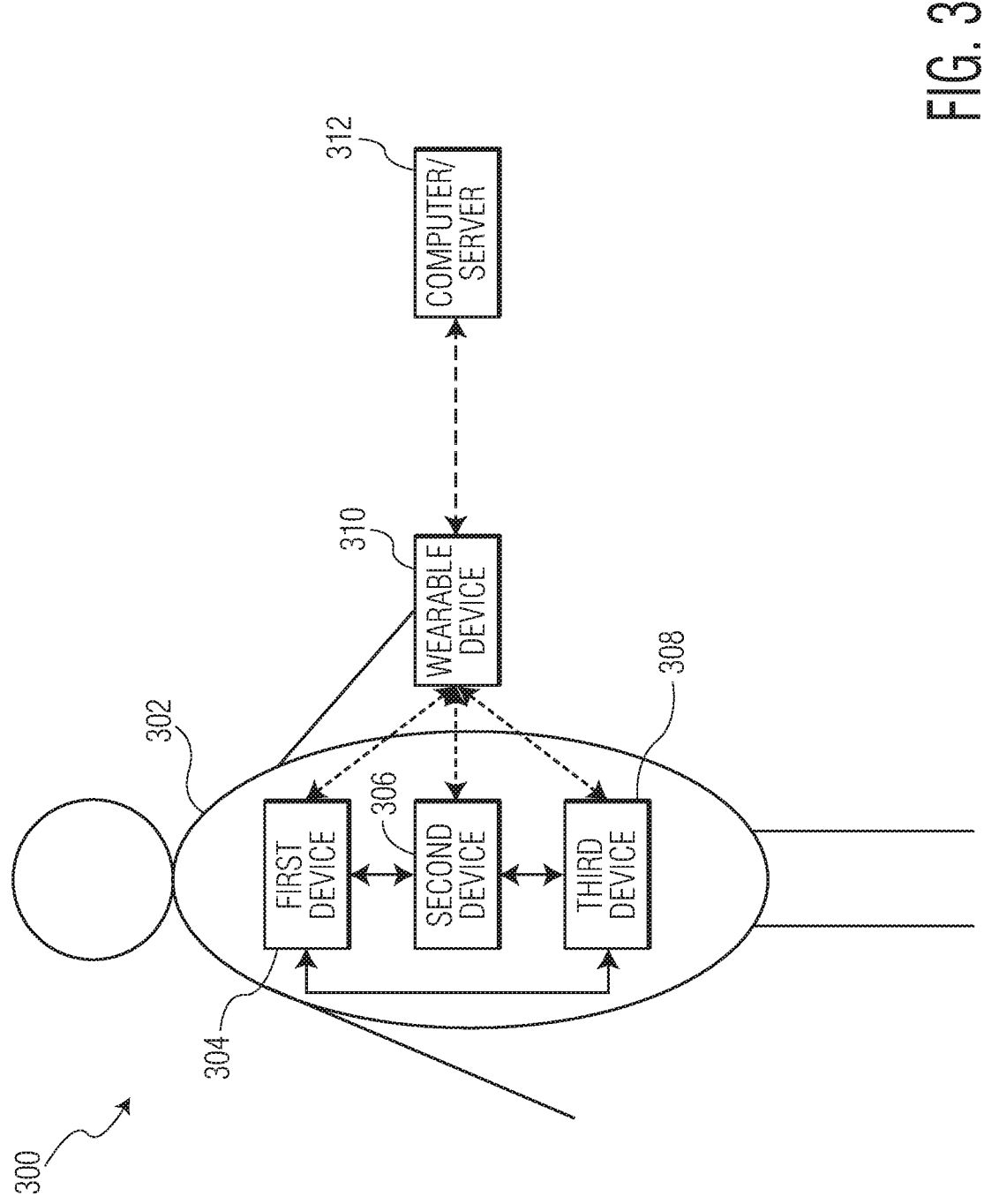
FIG. 3 is an example of first, second and third electromagnetic structural characterization devices on a biological structure.

FIG. 3 is an example 300 of first, second and third electromagnetic structural characterization devices on a biological structure. The example 300 includes a biological structure 302 (e.g. human body), a first device at a first location 304 (e.g. transmitter), a second device at a second location 306 (e.g. first receiver), a third device at a third location 308 (e.g. second receiver), a wearable device at a fourth location 310, and a computer/server at a fifth location 312.

The first device 304 generates and transmits a first electric field (E1) and a first magnetic field (H1) that are coupled to the biological structure 302 (e.g. human body). The second device 306 measures a second electric field (E2) and a second magnetic field (H2). The third device 308 measures a third electric field (E3) and a third magnetic field (H3).

These field measurements can then be communicated over a data communications interface (not shown) to wearable device 310. As mentioned, this data communication can use the same near-field antennas as the measurement field signals, and/or the fields can be modulated with the communications data.

The wearable device 310 can be a watch or monitoring device, and include a communication function and a controller function and a user interface.

A controller in the wearable device 310 (e.g. like controller 104) then analyzes field signals (E1, H1 and E2, H2) to determine a first path impedance between the first device 304 (e.g. transmitter) and the second device 306 (e.g. first receiver).

The controller also analyzes field signals (E1, H1 and E3, H3) to determine a second path impedance between the first device 304 (e.g. transmitter) and the third device 308 (e.g. second receiver). Thus multiple health conditions can be monitored at once.

The path impedances may individually or in combination prompt the controller in the wearable device 310 to generate one or more warnings or information displays to both the person (e.g. 302) and the computer/server 312.

Warnings or information sent to the computer/server 312 can be further evaluated by a local or remote medical provider, hospital, etc.

Figure 4:
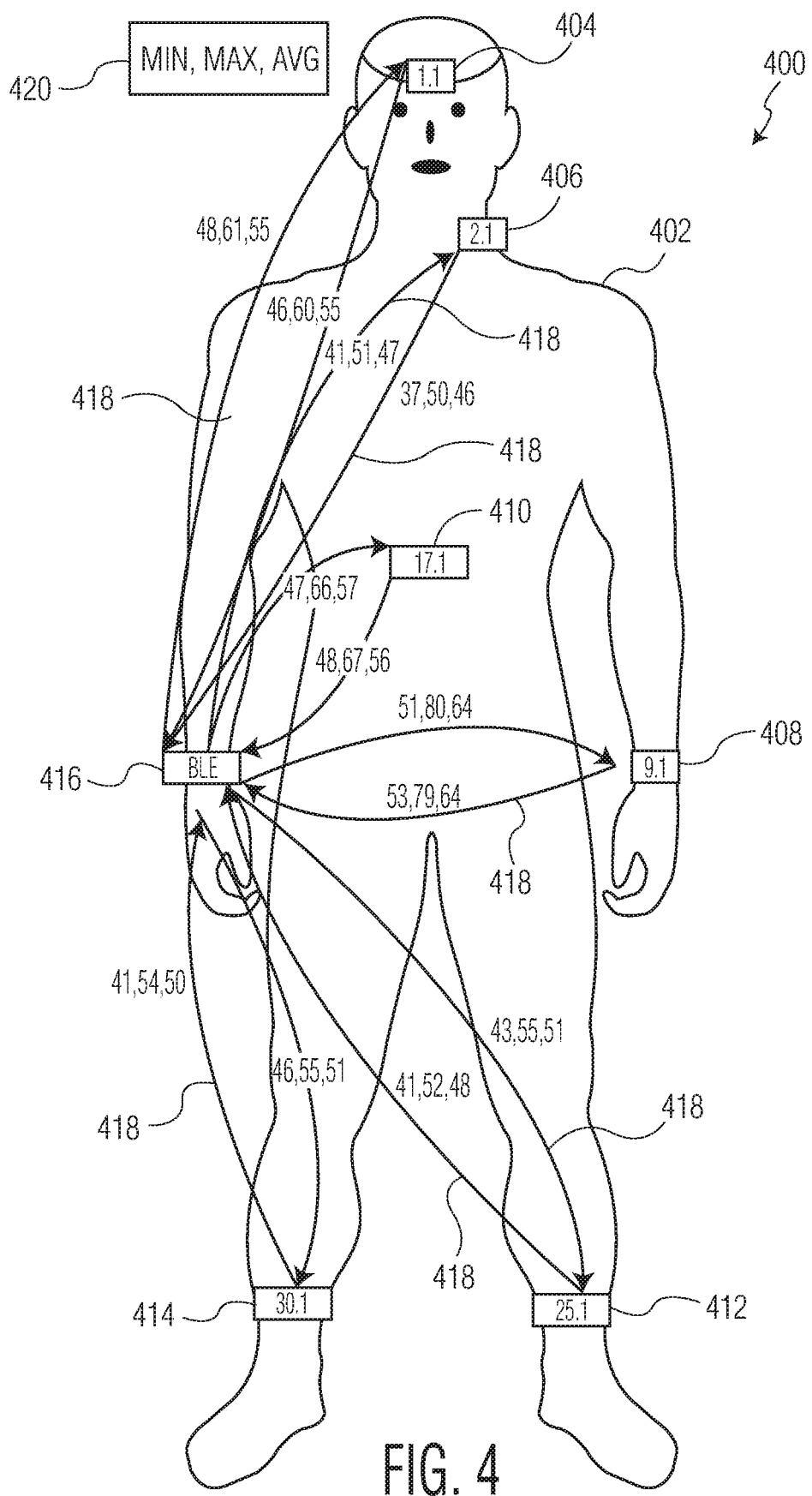
FIG. 4 is an example of a set of electromagnetic structural characterization devices on a biological structure.

FIG. 4 is an example 400 of a set of electromagnetic structural characterization devices on a biological structure. The example 400 includes a biological structure 402 (e.g. human body) and a set of devices coupled to the structure 402.

These are a first device 404 (1.1=forehead), a second device 406 (2.1=left side of the neck), a third device 408 (9.1=left wrist), a fourth device 410 (17.1=lower side of the chest), a fifth device 412 (25.1=left ankle), a sixth device 414 (30.1=right ankle), and a wearable device 416 (BLE—Bluetooth Low Energy).

Received signal strength indicator (RSSI) values 418 having minimum, maximum, average measurements 420 are collected in both directions. Both directions refer to when a pair of the devices exchange their transmitter/receiver roles.

Selection of the locations for these devices, in some example embodiments, provides an optimally accurate way for mapping the measured RSSI values 418 to different postures and movements of the structure 402.

Some of these postures/movements include:
stationary (arms down)
walking (arms down)
hands closed
hand over first device
hand over second device
arm (with first device) behind the back
arm (with first device) touching metal large object
twisting arm (with first device)

For these various postures/movements, the RSSI values 418 are recorded. The data communications link re-uses the same fields that measure the path impedance.

In some examples, the transmitted fields voltage is 130 dBμV at a frequency of 10.6 MHz. These measurements show that the path impedance (Zpath) and RSSI values 418 are dependent of the biological structure's 402 positioning/posture.

Using these multiple devices, a complete body map can be recorded and monitored over time for a patient in a medical context (e.g. alarm conditions, lack of physical movements after a surgery, etc.)

As mentioned earlier, these various postures/movements, the RSSI values 418 can also be used to control a user interface, perhaps on the wearable device 416 or another remote device at a greater distance from the structure 402.

For the example in FIG. 4, RSSI value 418 differences based on which device is functioning in a transmitter role or receiver role may be due to variations in measurement errors (e.g. tolerance) of the RSSI measurements (e.g. +/−2 dB). Alternatively since these RSSI values 418 were measured in an actual lab setting, a person acting as the structure 402 may have slightly moved between subsequent RSSI value 418 measurements.

Various functions, instructions, logic, firmware and the like discussed above, in some examples is implemented within the controller 104. The controller 104 in some example embodiments includes or is supported by other components, such as: an input/output data interface, a processor, a storage device, and a non-transient machine-readable storage medium. The machine-readable storage medium may include some or all of the instructions which control how the electromagnetic device 102 receives input data and transforms the input data into output data, using data within the storage device. In other example embodiments, the set of instructions and/or functionality described above can be implemented either using logic gates, application specific chips, firmware, as well as other hardware forms.

It will be readily understood that the components of the embodiments as generally described herein and illustrated in the appended figures could be arranged and designed in a wide variety of different configurations. Thus, the detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

What is claimed is:

1. A first device for electromagnetic structural characterization, comprising:
    a controller having a near-field electromagnetic transmitter and a communications interface, wherein the controller is configured to:
        send a near-field signal, over the near-field electromagnetic transmitter, that causes the near-field electromagnetic transmitter to generate both a first electrical near-field (E1) and a first magnetic near-field (H1),
        receive, over the communications interface, data representing a second electrical near-field (E2) and a second magnetic near-field (H2) received by a near-field electromagnetic receiver in a second device in response to the first electrical near-field (E1) and the first magnetic near-field (H1) generated by the first device, wherein the first electrical near-field (E1) and the first magnetic near-field (H1) correspond to when the near-field electromagnetic transmitter is configured to be at a first location proximate to a structure and the second electrical near-field (E2) and the second magnetic near-field (H2) correspond to when the near-field electromagnetic receiver of the second device is configured to be at a second location proximate to the structure,
        calculate a transmitted field impedance based upon E1/H1 and a received field impedance based upon E2/H2, and
        calculate a path impedance based upon a difference between the transmitted field impedance and the received field impedance and a factor depending upon the shape of or substances within the structure, wherein the path impedance is interpreted as a distance between the first location and the second location, and
    a user interface and the controller is configured to manipulate the user interface based on the path impedance.

2. The device of claim 1, wherein the distance corresponds to at least one of: a static structural orientation, a dynamic structural movement, a structural deformation, a body position, or a body movement.

3. The device of claim 1, wherein the controller configures the first electrical near-field (E1) and the first magnetic near-field (H1) to have a frequency that results in surface waves interacting over an exterior surface of the structure.

4. The device of claim 1, further comprising: performing the path impedance calculations based on absolute values of each field's signal strength.

5. The device of claim 1, wherein a variation in the path impedance over time is based on a change in the distance between the near-field electromagnetic transmitter in the first device and the near-field electromagnetic receiver in the second device and the change in the distance between the near-field electromagnetic transmitter and the near-field electromagnetic receiver is interpreted as a change in a posture of the structure, wherein the structure is a biological structure.

6. The device of claim 1, wherein the distance corresponds to physical motion either: after surgery, after a medical procedure, during sleep, while exercising, or during a routine activity.

7. The device of claim 1, wherein the path impedance is based on a set of substances within the structure.

8. The device of claim 7, wherein the substances correspond to at least one of: a liquid, a gas, a biological organ, a biological substance, or a tissue.

9. The device of claim 1, wherein the structure is a biological structure, a variation in the path impedance over time is based on a change in substances within the biological structure, and the change in the substances within the structure is based on a change in a health condition of an organ or tissue within the biological structure.

10. The device of claim 1, wherein the controller configures the first electrical near-field (E1) and the first magnetic near-field (H1) to have a frequency that penetrates the structure.

11. The device of claim 1, further comprising: performing the path impedance calculations based on both amplitude and phase values of each near-field's signal strength.

12. The device of claim 1, wherein the near-field electromagnetic transmitter in the first device includes an antenna system configured to generate the first magnetic near-field (H1) and the first electrical near-field (E1).

13. The device of claim 1, wherein the near-field electromagnetic receiver in the second device includes an antenna system configured to receive the second electric near-field (E2) and the second magnetic near-field (H2).

14. The device of claim 1, wherein both the first electrical near-field (E1) and the first magnetic near-field (H1) are NFEMI (near field electromagnetic induction) fields.

15. The device of claim 1, wherein either the near-field electromagnetic transmitter or near-field electromagnetic receiver include antennas that are capacitively, but not galvanically, coupled to the structure.

16. A first device for near-field electromagnetic structural characterization, the first device comprising a controller having a near-field electromagnetic receiver and a communications interface, wherein the controller is configured to:
receive, over the communications interface, data representing a first electrical near-field (E1) and a first magnetic near-field (H1) generated by a near-field electromagnetic transmitter in a first device,
receive, from the near-field electromagnetic receiver, a second electrical near-field (E2) and a second magnetic near-field (H2) received by a near-field electromagnetic receiver in a second device in response to the first electrical near-field (E1) and the first magnetic near-field (H1) generated by the first device, wherein the first electrical near-field (E1) and the first magnetic near-field (H1) correspond to when the near-field electromagnetic transmitter in the first device is configured to be at a first location proximate to a structure and the second electrical near-field (E2) and the second magnetic near-field (H2) correspond to when the near-field electromagnetic receiver in the second device is configured to be at a second location proximate to the structure,
calculate a transmitted field impedance based upon E1/H1 and a received field impedance based upon E2/H2, and
determine a path impedance based upon a difference between the transmitted field impedance and the received field impedance and a factor depending upon the shape of or substances within the structure, wherein the path impedance is interpreted as a distance between the first location and the second location,
a user interface and the controller is configured to manipulate the user interface based on the path impedance.

17. A first device for electromagnetic structural characterization, the first device comprising:
a near-field electromagnetic transmitter configured to generate a first electrical near-field (E1) and a first magnetic near-field (H1);
a communications interface configured to receive a second electrical near-field (E2) and a second magnetic near-field (H2) from a near-field electromagnetic receiver in a second device in response to the first electrical near-field (E1) and the first magnetic near-field (H1) generated by the first device;
a controller coupled to the near-field electromagnetic transmitter and the communications interface, wherein the first electrical near-field (E1) and the first magnetic near-field (H1) correspond to when the near-field electromagnetic transmitter in the first device is configured to be at a first location proximate to a structure and the second electrical near-field (E2) and the second magnetic near-field (H2) correspond to when the near-field electromagnetic receiver in the second device is configured to be at a second location proximate to the structure; and wherein the controller is configured to:
calculate a transmitted field impedance based upon E1/H1 and a received field impedance based upon E2/H2, and
determine a path impedance based upon a difference between the transmitted field impedance and the received field impedance and a factor depending upon the shape of or substances within the structure, wherein the path impedance is interpreted as a distance between the first location and the second location, and
a user interface and the controller is configured to manipulate the user interface based on the path impedance.

* * * * *